United States Patent [19]

Pettit et al.

[11] Patent Number: 5,352,804
[45] Date of Patent: Oct. 4, 1994

[54] ISOLATION AND STRUCTURE OF HALISTATIN 2

[75] Inventors: George R. Pettit, Paradise Valley; Feng Gao, Tempe, both of Ariz.

[73] Assignee: Arizona Board of Regents, a body corporate, acting on behalf of Arizona State University, Tempe, Ariz.

[21] Appl. No.: 4,852

[22] Filed: Jan. 19, 1993

[51] Int. Cl.$^5$ .......................................... C07D 323/00
[52] U.S. Cl. .................................................. 549/264
[58] Field of Search ................ 549/344, 264; 514/450, 514/908; 435/240.2

*Primary Examiner*—Nicky Chan
*Attorney, Agent, or Firm*—Richard R. Mybeck

[57] ABSTRACT

An intensive long-term investigation of marine organisms as sources of new anticancer drugs has led to the isolation and structural elucidation (primarily by high field NMR and mass spectrometry) of halistatin 2, a new polyether macrolide of the halipyran-type, from the Western Indian Ocean sponge *Axinella cf. carteri* (Dendy). Halistatin 2 ($1.4 \times 10^{-6}\%$ yield) caused the accumulation of cells arrested in mitosis, inhibited tubulin polymerization, and inhibited the binding of radiolabeled vinblastine and GTP to tubulino. Further, Halistatin 2 displayed significant activity against selected human tumor cell lines.

2 Claims, No Drawings

ISOLATION AND STRUCTURE OF HALISTATIN 2

Financial assistance for this project was provided by U.S. Government Grant No. OIG-CA 44344-01-A1-02 and the United States Government may own certain rights in this invention.

INTRODUCTION

This invention relates generally to a newly discovered compound which is found to inhibit the growth of various selected human cell lines tumors by the National Cancer Institute. More specifically, this invention relates to a new polyether macrolide of the halipyran-type which was isolated from the Western Indian Ocean sponge *Axinella carteri* and which has been found to cause the accumulation of cells arrested in mitosis, the inhibition of tubulin polymerization, the inhibition of the binding of radiolabeled vinblastine and GTP to tubulin and which demonstrates effective neoplastic activity against various human tumor cells.

BACKGROUND OF THE INVENTION

A great number of ancient marine invertebrate species in the Phyla Bryozoa, Mollusca and Porifera were well established in the earth's oceans over one billion years ago. Certainly such organisms had explored trillions of biosynthetic reactions in their evolutionary chemistry to reach present levels of cellular organization, regulation and defense. Marine sponges have changed minimally in physical appearance for nearly 500 million years, suggesting a very effective chemical evolution in response to changing environmental conditions for at least that time period. Some recognition of the potential for utilizing biologically potent marine animal constituents was recorded in Egypt about 2,700 BC, and by 200 BC sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and/or cytotoxic agents. Analogous considerations suggested that marine organisms could also provide effective new drugs for other severe medical challenges, such as viral diseases. Furthermore, marine organisms were expected to contain potentially useful drug candidates (and biochemical probes) of unprecedented structural types, that would have eluded discovery by contemporary techniques of medicinal chemistry. Fortunately, some of these expectations have been realized in the intervening period. Illustrative of these successes are the discoveries of the bryostatins, dolastatins, and cephalostatins by the Cancer Research Institute in Tempe, Ariz. where several members of these series of remarkable anticancer drug candidates are either now in human clinical trial or preclinical development. See U.S. Pat. Nos. 4,816,444, 4,833,257, 4,873,245, and 4,879,278.

As is well known to those presently engaged in medical research, the time between the isolation of a new compound, and its introduction to the market place takes at least several years in the best case and can take several decades. Consequently, industry, in association with the government, has devised a number of qualifying tests which serve two purposes. One purpose is to eliminate those substances whose results in the qualifiers unequivocally demonstrate that the further expenditure of funds on developing those substances would be economically counterproductive. The second, and more important purpose, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such data approaches Ten Million Dollars ($10,000,000 U.S.) per substance. Economics dictate that such an investment not be made unless there is a reasonable likelihood that it can be recovered. Absent such an opportunity, there will be no such investment, and without investment, the research requisite for the discovery of potentially life saving drugs will stop.

Only two hundred years ago, many diseases ravaged humankind. Many of these diseases now have been controlled or eradicated. In the development of the means to treat or control these diseases, work with the appropriate common experimental animals was of critical importance. With the various types of cancers, and with the HIV virus, such work is presently ongoing. The research for the treatment of various types of cancer is coordinated in the United States by the National Cancer Institute (NCI). NCI, as a government entity, has been charged with assisting anti-cancer research. To establish whether a substance has anti cancer activity, NCI has established a variety of protocols, one of which involves testing the candidate substance against a cell line panel containing 60 human tumor cell lines. This protocol has been verified and is generally accepted throughout the scientific community. This protocol and the established statistical means of evaluating the results obtained therefrom have been fully described in the literature. See *Principles & Practice of Oncology* PPO Updates, Volume 3, Number 10, Oct. 1989, by Michael R. Boyd, M.D., Ph.D., for an indepth description of the test protocol. The statistical analysis is explained in "Display and Analysis of Patterns of Differential Activity of Drugs Against Human Tumor Cell Lines: Development of Means Graph and COMPARE Algorithm" *Journal of the National Cancer Institute* Reports Vol. 81, No. 14, Pg. 1088, Jul. 14, 1989, by K. D. Paull et al. Both of these references are incorporated herein by this reference thereto.

The Constitution of the United States (Art. 1, Sec. 8) authorizes Congress to establish the United States Patent and Trademark Office (USPTO) to promote scientific advancement. This obligation can only be fully met when the USPTO accepts current medical and scientific realities in the area of medical research.

The Framers of the Constitution meant to advance scientific advancement. Cells are alive. The impairment of human tumor cell growth is utility. The sole right obtained from the grant of Letters Patent is the right to prevent others from exploiting the subject matter of the patent. The recognition of cell line data as a measure of antineoplastic activity and therefor an acceptable showing of "utility" can aid research in the United States, and thereby save the citizens of the United States from being held hostage by foreign governments or foreign corporations, if such research is no longer viable in the United States.

Numerous compounds have been discovered which demonstrate significant antineoplastic activity. As discussed above, many of these compounds have been extracted, albeit with great difficulty, from living creatures such as the sponge or the sea hare. However, once the isolation and testing of such compounds has progressed, a practical problem exists, namely, how to obtain a significant quantity of the compound.

Unlike cinchona bark which is collected to produce quinine and has an excellent yield, the collection and processing of the compounds of the present invention in the natural occurring state ranges from the grossly impractical to the utterly impossible. Even ignoring potential ecological effects, the population of such creatures is clearly insufficient. Accordingly, the elucidation of the absolute structure of such antineoplastic compounds is essential.

A major component of vigorous efforts for over two decades has been directed at marine sponge antineoplastic and/or cytotoxic biosynthetic products. A number of unusual polyether macrolides, peptides and heterocyclic compounds have been uncovered. These efforts included the now disclosed isolation and structural elucidation of a new, strongly cytotoxic macrolide herein denominated "halistatin 2".

BRIEF SUMMARY OF THE INVENTION

An intensive long-term investigation of marine organisms as sources of new anticancer drugs has led to the isolation and structural elucidation (primarily by high field NMR and mass spectrometry) of a new polyether macrolide of the halipyran-type, from the Western Indian Ocean sponge *Axinella carteri* (Dendy) halistatin 2. Halistatin 2 ($1.4 \times 10^{-6}\%$ yield) caused the accumulation of cells arrested in mitosis, inhibited tubulin polymerization, and inhibited the binding of radiolabeled vinblastine and GTP to tubulin and was found to have the structure shown below.

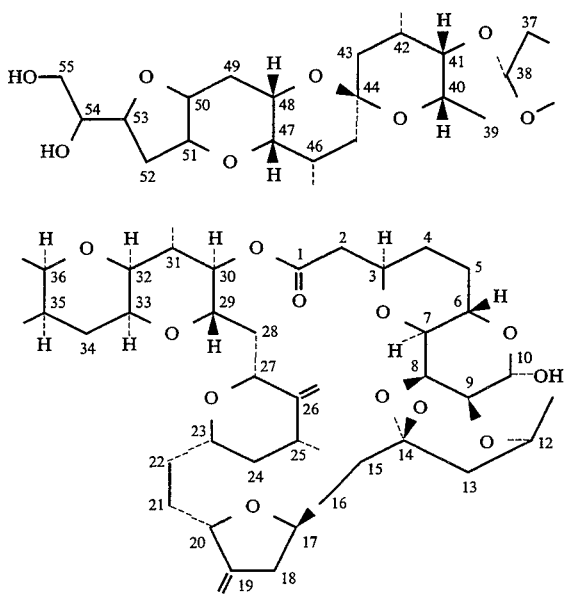

The averaged negative $\log_{10} GI_{50}$ values obtained for each cell line with halistatin 2 in the present study are provided as follows, along with the individual cell line identifiers: CCRF-CEM (9.70), HL-60TB (9.80), K-562 (9.64), MOLT-4 (9.39), RPMI-8226 (9.39), SR (9.67); A549/ATCC (8.74), EKVX (8.39), HOP-18 (8.55), HOP-62 (9.16), HOP-92 (8.92), NCI-H226 (9.14), NCI-H23 (9.18), NCI-H322M (8.52), NCI-H460 (9.42), NCI-H522 (9.70), LXFL 529 (9.35); DMS 114 (9.47), DMS 273 (9.89); COLO 205 (9.66), DLD-1 (8.92), HCC-2998 (8.89), HCT-116 (9.26), HCT-15 (8.26), HT29 (9.34), KM12 (9.27), KM20L2 (9.37), SW-620 (9.40); SF-268 (8.74), SF-295 (9.74), SF-539 (9.49); SNB-19 (8.68), SNB-75 (9.57), SNB-78 (9.92), U251 (9.32), XF 498 (9.37); LOX IMVI (9.30), MALME-3M (9.64), M14 (9.17), M19-MEL (9.51), SK-MEL-2 (9.51), SK-MEL-28 (9.00), SK-MEL-5 (9.74), UACC-257 (8.64), UACC-62 (9.47); IGROV-1 (9.05), OVCAR-3 (9.55), OVCAR-4 (8.11), OVCAR-5 (8.74), OVCAR-8 (8.89), SK-OV-3 (9.17); 786-0 (9.41), A498 (8.74), ACHN (8.36), CAKI-1 (8.89), RXF-393 (9.32), SN12C (8.74), TK-10 (8.26), UO-31 (8.22).

Accordingly, a principal object of the present invention is the isolation of a new polyether macrolide denominated "halistatin 2" having antimitotic properties.

Another object of the present invention is the structural elucidation of the substance denominated "halistatin 2".

These and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENT

The sponge, Porifera, *Axinella cf. carteri* (Dendy) (Axinellida), referred to in this application was first identified by the Curator of Invertebrate Zoology, Dr. Klaus Reutzler at the National Museum of Natural History, Smithsonian Institution.

The collection site for this sponge was in the Comoros in the West Indian Ocean and a specimen is on deposit at the ARIZONA STATE UNIVERSITY/CANCER RESEARCH INSTITUTE ("ASU/CRI"). The museum specimen is coded M-5301, B725014 and preserved in alcohol. ASU/CRI has a CITES permit (Convention on International Trade in Endangered Species of Wild Fauna and Flora) authorizing them to receive and store preserved, dried or embedded specimens, and follow the requirements established by the regulations.

A 1989 collection (600 kg. wet wt) of the erect orange sponge *Axinella carteri* (in methanol) was made. It was extracted with methanol-dichloromethane, and the chlorocarbon fraction was partitioned in methanol-water (9:1→3:2) between hexane→dichloromethane. The resulting PS cell line active ($ED_{50}$ 0.30 μg/ml) dichloromethane fraction was then separated by a series of gel permeation and partition column chromatographic steps on SEPHADEX LH-20, followed by HPLC on RP-8 reversed phase silica gel in accordance with Scheme 1 shown below.

The bioassay (PS cell line) guided separation of *Axinella cf carteri* afforded ($1.4–10^{-6}\%$ yield) the new and very active macrolide halistatin 2 having the following structure:

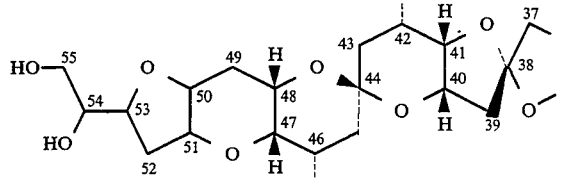

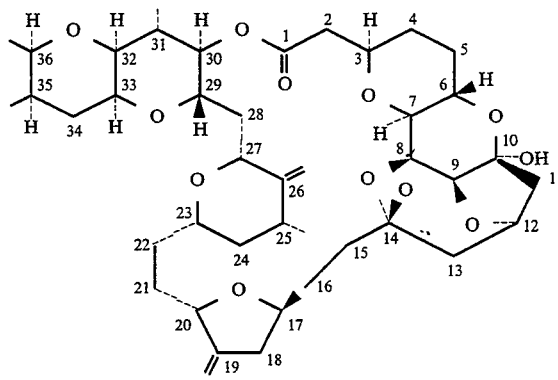

The structure of halistatin 2 was assigned on the basis of 2D NMR and other spectroscopy data. The IR spectrum of halistatin 2 indicated absorptions corresponding to hydroxyl groups, an ester carbonyl and double bonds at respectively 3358, 1734 and 1653 cm$^{-1}$. The FABMS of halistatin 2 suggested a molecular formula of $C_{61}H_{86}O_{20}$, using the peak at m/z 1145 [M+Li]$^+$ as corresponding to a calculated molecular weight of 1138.

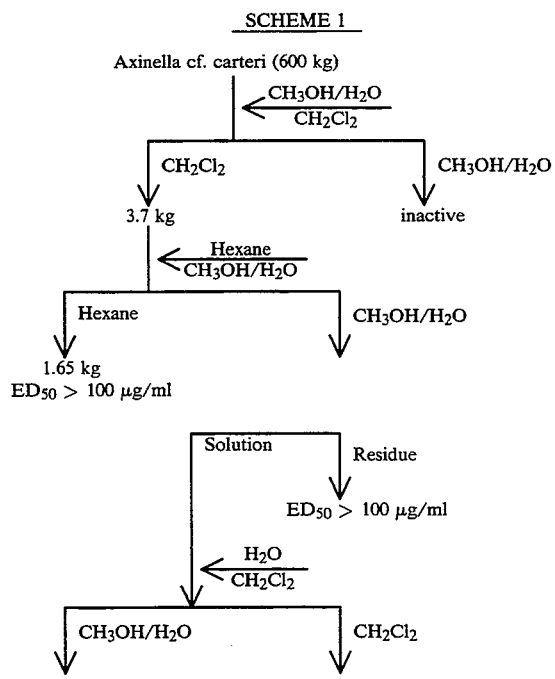

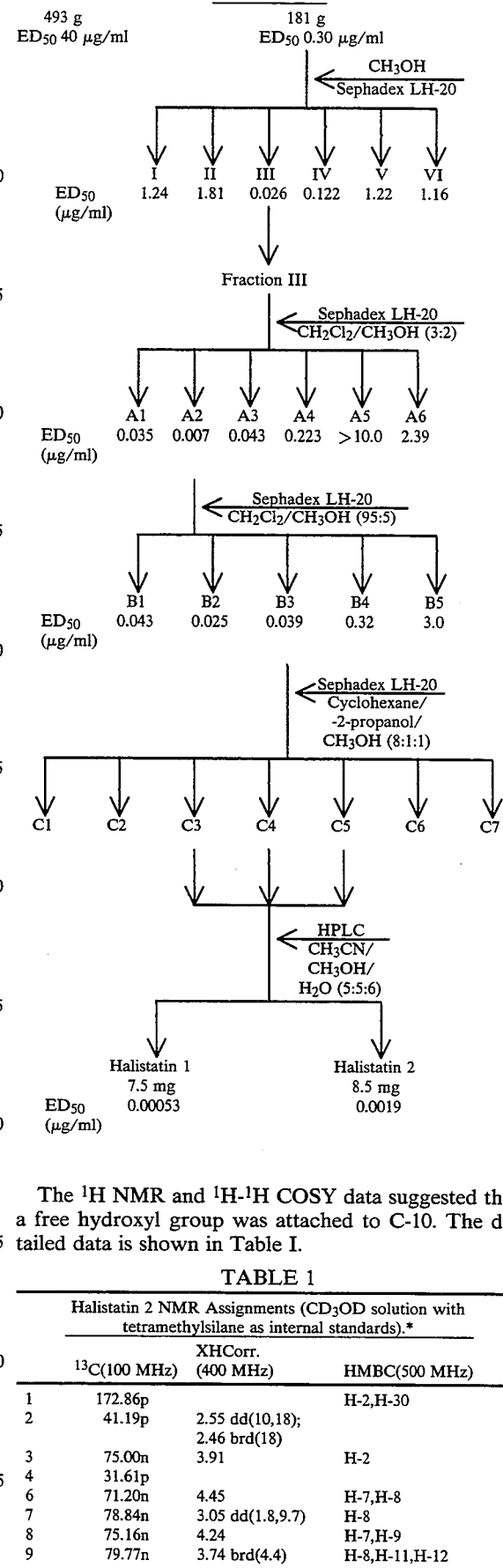

The $^1$H NMR and $^1$H-$^1$H COSY data suggested that a free hydroxyl group was attached to C-10. The detailed data is shown in Table I.

TABLE 1

| | Halistatin 2 NMR Assignments (CD$_3$OD solution with tetramethylsilane as internal standards).* | | |
|---|---|---|---|
| | $^{13}$C(100 MHz) | XHCorr. (400 MHz) | HMBC(500 MHz) |
| 1 | 172.86p | | H-2,H-30 |
| 2 | 41.19p | 2.55 dd(10,18); 2.46 brd(18) | |
| 3 | 75.00n | 3.91 | H-2 |
| 4 | 31.61p | | |
| 6 | 71.20n | 4.45 | H-7,H-8 |
| 7 | 78.84n | 3.05 dd(1.8,9.7) | H-8 |
| 8 | 75.16n | 4.24 | H-7,H-9 |
| 9 | 79.77n | 3.74 brd(4.4) | H-8,H-11,H-12 |

TABLE 1-continued

Halistatin 2 NMR Assignments (CD$_3$OD solution with tetramethylsilane as internal standards).*

| | $^{13}$C(100 MHz) | XHCorr. (400 MHz) | HMBC(500 MHz) |
|---|---|---|---|
| 10 | 103.75p | | H-8,H-9,H-11,H-12 |
| 11 | 87.64n | 4.25 | H-9,H-12,H-13 |
| 12 | 82.29n | 4.73 t(4.6) | H-9,H-11,H-13 |
| 13 | 49.00p | 2.13;1.96 dd(5,13) | |
| 14 | 110.83p | | H-8,H-11,H-12,H-13 |
| 16 | 29.37p | 2.17;1.40 | H-18 |
| 17 | 77.18n | 4.07 | H-18 |
| 18 | 39.75p | 2.80 brm;2.32 | H-19a |
| 19 | 153.16p | | H-18,H-17,H-19a |
| 19a | 105.65p | 5.05 brs;5.00 brs | H-18 |
| 20 | 76.07n | 4.45 | H-19a |
| 23 | 75.45n | 3.69 brt(10) | |
| 24 | 44.96p | 1.72;1.02 | H-25a |
| 25 | 37.22n | 2.32 | H-25a,H-24,H-26a |
| 25a | 18.41n | 1.08 d(6.4) | H-24 |
| 26 | 153.32p | | H-27,H-25,H-25a,H-24 H-26a |
| 26a | 104.79p | 4.86 brs;4.80 brs | H-27,H-28 |
| 27 | 75.07n | 3.60 | H-29,H-26a |
| 28 | 37.90p | 2.25;1.80 | H-29,H-30 |
| 29 | 73.78n | 4.23 | H-27,H-25 |
| 30 | 77.56n | 4.62 dd(4.7,7.6) | H-29,H-31a |
| 31 | 37.50n | 2.05 | H-29,H-31a |
| 31a | 15.76n | 1.04 d(7.1) | H-30,H-31,H-32 |
| 32 | 78.20n | 3.20 dd(4.9,6.7) | H-30,H-31a,H-33 |
| 33 | 65.95n | 3.88 | H-29,H-32 |
| 34 | 30.85p | 2.04;1.80 | H-33,H-36 |
| 35 | 76.34n | 4.10 | H-36 |
| 36 | 78.01n | 4.10 | H-35 |
| 37 | 45.51p | 2.39;2.00 | |
| 38 | 114.78p | | H-36,H-37,H-39,H-40 |
| 39 | 44.84p | 2.30;2.30 | |
| 40 | 72.31n | 3.94 brs | H-39,H-41 |
| 41 | 81.06n | 3.65 brt(2.8) | H-42a,H-39 |
| 42 | 27.15n | 2.36 | H-42a,H-43 |
| 42a | 18.18n | 0.94 d(7.0) | H-43 |
| 43 | 38.09p | 1.43;1.33 | H-42a,H-41 |
| 44 | 98.14p | | H-43 |
| 45 | 38.17p | | H-46a,H-47 |
| 46 | 30.14n | 2.18 | H-46a,H-47 |
| 46a | 17.65n | 0.93 d(6.8) | H-47 |
| 47 | 74.57n | 3.11 brd(2.2) | H-46a |
| 48 | 65.31n | 3.57 | H-47 |
| 49 | 32.03p | 2.10;1.92 | H-48 |
| 50 | 75.81n | 3.86 | H-48,H-51 |
| 51 | 78.44n | 4.01 brs | H-47,H-50 |
| 52 | 37.29p | 2.02; | |
| 53 | 79.87n | 4.24 | H-55,H-51 |
| 54 | 75.16n | 3.49 brdd(5.5,10) | H-55 |
| 55 | 65.18p | 3.56 brs;3.56 brs | |

Refer to (Hz) for the coupling constants. Both n and p indicate APT results. The $^{13}$C NMR signal for the C-13 was overlapped with solvent signals. Some of the coupling patterns and/or coupling constants were not measured due to overlapping. The other four unassigned $^{13}$C NMR signals were at δ 30.09: 31.47: 33.06 and 35.92 for C-5; C-15; C-21 and C-22.

For example, the signal at δ 4.73 (triplet, J=4.6 Hz, H-12) was coupled with a signal at δ 4.25 (H-11) and an upfield signal at 1.96 (H-13). A signal at δ 4.24 (H-8) was coupled with a broadened doublet signal at δ 3.74 (H-9), which showed long range coupling with the signal at δ 4.25 (H-11).

In the $^{13}$C NMR spectrum, sixty-one carbon signals from halistatin 2 were observed. Among these signals, four were hemiacetal at δ 103.75 (C-10), 110.83 (C-14), 114.78 (C-38) and 98.14 ppm (C-44), as elucidated by the $^1$H-$^{13}$C correlation and APT spectra. The C-1 to C-14 signals of halistatin 2 were very similar to the C-1 to C-14 signals of halistatin 1. In agreement with the assigned structure, 18 methylene group signals were observed arising from halistatin 2 in the δ 50 to 28 ppm region of the $^{13}$C NMR spectrum. Moreover, interpretation of the HMBC spectrum shown in Table 1 strongly supports the assigned structure shown below.

The hemiacetal signal at δ 103.75 (C-10) showed cross peaks with the H-8, H-9, H-11 and H-12 signals and the C-14 carbon signal at δ 110.83 showed cross peaks with the H-8, H-11, H-12 and H-13 signals. The C-10 hydroxyl group was assigned the α-orientation on the basis of optical rotation ($[\alpha]_D^{25} - 59°$) and the nOe difference spectroscopy results as shown in Table 2.

TABLE 2

The nOe difference spectroscopy interpretation for halistatin 2. The spectra were recorded in CD$_3$OD.

| Signals Irradiated | Signals enhanced (Halistatin 2) |
|---|---|
| H-7 | H-9,H-8 |
| H-9 | H-7 |
| H-12 | H-11,H-13 |
| H-18 | H-17 |
| H-25a | H-26a |
| H-30 | H-31a,H-28 |
| H-31a | H-26a |
| H-32 | H-31a |

Halistatin 2, demonstrated significant cytotoxic potency (e.g., GI$_{50}$ ~7×10$^{-10}$M) when evaluated in the NCI in vitro primary screen. Analysis demonstrated that the screening profile of halistatin 2 was characteristic of a general mechanistic class of tubulin-interactive antimitotics. This class includes such diverse agents as the known clinically active antitumor drugs, vincristine, vinblastine and taxol, as well as new investigational drugs such as dolastatin 10.

Halistatin 2 was evaluated to determine if it was an antimitotic agent which interfered with the polymerization of purified tubulin and microtubule assembly dependent on microtubule-associated proteins isolated.

With L1210 murine leukemia cells halistatin 2 had significant cytotoxicity (IC$_{50}$ value of 0.4), and caused a significant rise in the mitotic index at cytotoxic concentrations, reaching values as high as 20%. In the glutamate-induced polymerization of purified tubulin, halistatin 2 had an IC$_{50}$ value of 4.9±0.5 μM. Halistatin 2 was shown to be a noncompetitive inhibitor of the binding of radiolabeled vinblastine to tubulin and to inhibit nucleotide exchange on tubulin. Halistatin 2 was superior as an inhibitor of nucleotide exchange at 5 and 10 μM, and inhibited the binding of radiolabeled vinblastine to tubulin by 51% and 75% at the two concentrations. For radiolabeled GTP binding to tubulin, the same drug concentrations inhibited the reaction by 17% and 51% with halistatin 2.

Attention will now be directed in the following paragraphs to the extraction and isolation of halistatin 2 from *Axinella carteri* and the biological test data obtained when freshly isolated halistatin 2 was tested by the NCI primary screen.

Sponge Extraction and Solvent Partition—The methanol shipping solution from approximately 600 kg (wet wt.) of *Axinella carteri* was decanted and to the solution was added an equal volume of dichloromethane (~600 l) and enough (10-20% by volume) water to provide two phases. The dichloromethane layer was separated and solvent evaporated in vacuo to yield the first extract (1.43 kg). To the sponge was added 1:1 dichloromethane-methanol (550 l.). After 28 days water (15% by volume) was added to produce a chlorocarbon phase which was separated and concentrated (in vacuo) to obtain the second extract (1.66 kg). Recovered dichloromethane was combined with the upper layer (methanol/water) to form a dichloromethane-methanol-water solvent mixture (approximately 2:3.8:1.2) that was returned to the sponge to obtain the third dichloromethane extract fraction (607 g) in an analogous manner (18–32 day extraction periods). The combined dichloromethane extract (3.7 kg) was dissolved in a mixture (20 l. each) of hexane and 9:1 methanol-water and extracted (six times) with hexane in a 55 l steel container. The hexane fraction was concentrated at 30° C. and then the temperature was raised to 50° C. to remove water. The dark oily residue weighed 1.65 kg. The 9:1 methanol-water solution was filtered (filter paper) and the tan precipitate collected ($ED_{50}$ > 100 μg/ml). The solution was diluted to 3:2 by adding 12 l. of water and extracted with dichloromethane (20 l., 3×). Concentration in vacuo gave a 181 g fraction from the chlorocarbon extract and a 493 g fraction from the methanol-water. Bioassay results (PS $ED_{50}$ 0.30 μg/ml pointed to the dichloromethane residue as the repository of the antineoplastic constituents. The PS cell line active fraction (181 g) was subjected to separation by gel permeation through a SEPHADEX LH-20 column (15×120 cm) packed in methanol. The column was eluted with methanol (25 l.) and fractions were monitored by the P388 cell line bioassay. The active fractions (3) were added to the top of another SEPHADEX LH-20 column (9×92 cm) in dichloromethane-methanol (3:2) and eluted with the same solvent. Active fractions were further separated by SEPHADEX LH-20 column (4.5×80 cm) partition chromatography using 95:5 dichloromethane-methanol as eluent. The resulting active fraction was next separated on a SEPHADEX LH-20 column (2.5×40 cm) using the solvent system 8:1:1 cyclohexane-isopropanolmethanol. Final separation and purification procedures utilized HPLC to provide 8.5 mg ($1.4 \times 10^{-6}$% yield) of halistatin 2. Halistatin 2 was isolated as an amorphorous solid melting at 194°–198° C. (Kofler-type hot stage): $[\alpha]_D^{25} -59°$ (C=0.48, $CH_3OH$); FABMS m/z 1139 $[M+H]^+$ ($C_{61}H_{86}O_{20}$=1138), 1121 $[M-H_2O+H]^+$; HRFABMS m/z 1145.5871 $[M+Li]^+$, calc for $C_{61}H_{86}O_{20}Li$ 1145.5872; and IR: $\nu_{max}$ (NaCl film) 3358 (OH), 1734 (COOR), 1653 (C=C), 1186, 1132, 1078, 1022.

Solvents used for column chromatography were redistilled. SEPHADEX LH-20, particle size 25–100 μm, used in column chromatographic separation was obtained from Pharmacia Fine Chemicals AB, Uppsala, Sweden. The TLC plates were from Analtech, Inc. The TLC plates were viewed under short wave (250 nm) uv-light first and then sprayed with ceric sulfate in 3N sulfuric acid followed by heating at approximately 150° C. For HPLC separations, the following conditions were used: PHENOMENEX PREPEX RP-8 Reverse Phase semi preparative column (10.0×250 mm, particle size 5–20μ); acetonitrile-methanol-water (5:5:6) as eluting solvent: ALTEX 110A pump controlled by AXXIOM micro computer; RAININ RI-1 refractive index detector, range 32, and time constant 0.25. The flow rate (0.8 or 1.0 ml/min) and sample (1.0 to 4.0 mg) injection varied as noted. The $^1H$-NMR, APT, $^1H$-$^1H$ COSY, $^1H$-$^{13}C$ COSY, nOe and $^{13}C$-NMR experiments were carried out using a BRUKER AM-400 NMR spectrometer equipped with cryomagnet and ASPECT-3000 computer. The HMBC spectra were recorded with a VARIAN 500 NMR spectrometer. The optical rotations were measured with a PERKIN-ELMER 241 polarimeter.

Biological Testing; Data Display and Analysis; Screening Data Summary. Freshly isolated halistatin 2 was tested in the NCI's human tumor, disease-oriented in vitro primary screen, and data calculations performed. Table 3 is a composite prepared from mean graphs constructed from the averaged $GI_{50}$ values from quadruplicate screenings of Halistatin 2. The overall panel mean $GI_{50}$ value was $6.8 \times 10^{-10}$M halistatin 2; standard errors averaged less than 10% of the respective means.

Halistatin 2, when tested against P388 lymphocytic leukemia in vivo resulted in a 100% survival rate at 40 μg/kg host body weight in BDF mice using NCI protocol as described by Geran et al (1972) *Cancer Chemotherapy Reports*, Part 3, 3, pp. 1–103, resulted in an 18% cure rate and 220% life extension of those note cured. When BDF, mice were treated with 40 μg/kg host body weight of halistatin 2.

The averaged negative $log_{10} GI_{50}$ values obtained for each cell line with halistatin 2 in the present study are provided as follows, along with the individual cell line identifiers: CCRF-CEM (9.70), HL-60TB (9.80), K-562 (9.64), MOLT-4 (9.39), RPMI-8226 (9.39), SR (9.67); A549/ATCC (8.74), EKVX (8.39), HOP-18 (8.55), HOP-62 (9.16), HOP-92 (8.92), NCI-H226 (9.14), NCI-H23 (9.18), NCIH-322M (8.52), NCI-H460 (9.42), NCI-H522 (9.70), LXFL 529 (9.35); DMS 114 (9.47), DMS 273 (9.89); COLO 205 (9.66), DLD-1 (8.92), HCC-2998 (8.89), HCT-116 (9.26), HCT-15 (8.26), HT29 (9.34), KM12 (9.27), KM20L2 (9.37), SW-620 (9.40); SF-268 (8.74), SF-295 (9.74), SF-539 (9.49); SNB-19 (8.68), SNB-75 (9.57), SNB-78 (9.92), U251 (9.32), XF 498 (9.37); LOX IMVI (9.30), MALME-3M (9.64), M14 (9.17), M19-MEL (9.51), SK-MEL-2 (9.51), SK-MEL-28 (9.00), SK-MEL-5 (9.74), UACC-257 (8.64), UACC-62 (9.47); IGROV1 (9.05), OVCAR-3 (9.55), OVCAR-4 (8.11), OVCAR-5 (8.74), OVCAR-8 (8.89), SK-OV-3 (9.17); 786-0 (9.41), A498 (8.74), ACHN (8.36), CAKI-1 (8.89), RXF-393 (9.32), SN12C (8.74), TK-10 (8.26), UO-31 (8.22).

As shown in Table 3, the individual cell line identifiers are grouped; by the operative diagnosis of the human patient from whom the cancer cells were taken, namely leukemia, non-small cell lung cancer, small cell lung cancer, colon cancer, central nervous system (CNS) or brain cancer, melanoma, ovarian cancer and renal cancer. As is apparent from the data displayed in Table 3, the potency of halistatin 2 against leukemia, small cell lung cancer, colon cancer, CNS cancer, and melanoma is especially noteworthy.

TABLE 3

| Panel/Cell Line | Activity of Halistatin 2 | | | |
|---|---|---|---|---|
| | $Log_{10}$ GI50 | GI50 | $Log_{10}$ TGI | TGI |
| Leukemia | | | | |
| CCRF-CEM | −9.70 | | −8.37 | |
| HL-60(TB) | −9.80 | | −9.00 | |
| K-562 | −9.64 | | −8.59 | |

TABLE 3-continued

| Panel/Cell Line | Log₁₀ GI50 | Activity of Halistatin 2 GI50 | Log₁₀ TGI | TGI |
|---|---|---|---|---|
| MOLT-4 | −9.39 | | −8.00 | |
| RPMI-8226 | −9.39 | | −8.00 | |
| SR | −9.38 | | −8.00 | |
| SR | −9.96 | | −8.68 | |
| Non-Small Cell Lung Cancer | | | | |
| A549/ATCC | −8.74 | | −8.00 | |
| EKVX | −8.39 | | −8.00 | |
| HOP-18 | −8.55 | | −8.00 | |
| HOP-62 | −9.16 | | −8.12 | |
| HOP-92 | −8.92 | | −8.00 | |
| NCI-H226 | −9.14 | | −8.43 | |
| NCI-H23 | −9.18 | | −8.17 | |
| NCI-H322M | −8.52 | | −8.00 | |
| NCI-H460 | −9.42 | | −8.17 | |
| NCI-H522 | −9.70 | | −9.26 | |
| LXFL529 | −9.35 | | −8.00 | |
| Small Cell Lung Cancer | | | | |
| DMS 114 | −9.47 | | −8.72 | |
| DMS 273 | −9.89 | | −8.26 | |
| Colon Cancer | | | | |
| COLO 205 | −9.66 | | −8.82 | |
| DLD-1 | −8.92 | | −8.00 | |
| HCC-2998 | −8.89 | −8.28 | | |
| HCT-116 | −9.26 | | −8.00 | |
| HCT-15 | −8.26 | | −8.00 | |
| HT29 | −9.34 | | −8.43 | |
| KM12 | −9.27 | | −8.00 | |
| KM2012 | −9.37 | | −8.72 | |
| SW-620 | −9.40 | | −8.00 | |
| CNS Cancer | | | | |
| SF-268 | −8.74 | | −8.00 | |
| SF-295 | −9.74 | | −8.28 | |
| SF-539 | −9.49 | | −8.82 | |
| SNB-19 | −8.68 | | −8.00 | |
| SNB-75 | −9.57 | | −8.00 | |
| SNB-78 | −9.92 | | −8.00 | |
| U251 | −9.32 | | −8.03 | |
| XF498 | −9.37 | | −8.35 | |
| Melanoma | | | | |
| LOX IMVI | −9.30 | | −8.34 | |
| MALME-3M | −9.64 | | −8.00 | |
| M14 | −9.17 | | −8.24 | |
| M19-MEL | −9.48 | | −8.30 | |
| SK-MEL-2 | −9.51 | | −8.34 | |
| SK-MEL-28 | −9.00 | | −8.00 | |
| SK-MEL-5 | −9.74 | | −8.74 | |
| UACC-257 | −8.64 | | −8.00 | |
| UACC-62 | −9.47 | | −8.00 | |
| Ovarian Cancer | | | | |
| IGROV1 | −9.05 | | −8.00 | |
| OVCAR-3 | −9.55 | | −8.80 | |
| OVCAR-4 | −8.11 | | −8.00 | |
| OVCAR-5 | −8.74 | | −8.00 | |
| OVCAR-8 | −8.89 | | −8.15 | |
| SK-OV-3 | −9.17 | | −8.00 | |
| Renal Cancer | | | | |
| 786-0 | −9.41 | | −8.00 | |
| A498 | −8.74 | | −8.00 | |
| ACHN | −8.36 | | −8.00 | |
| CAKI-1 | −8.89 | | −8.00 | |
| RXP-393 | −9.32 | | −8.51 | |
| SN12C | −8.74 | | −8.00 | |
| TK-10 | −8.26 | | −8.00 | |
| UO-31 | −8.22 | | −8.00 | |
| MG_MID | −9.17 | | −8.21 | |
| Delta | 0.79 | | 1.05 | |
| Range | 1.85 | | 1.26 | |

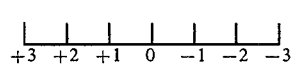
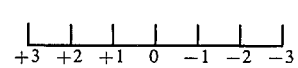

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A composition of matter denominated halistatin 2 and having the following structural formula:

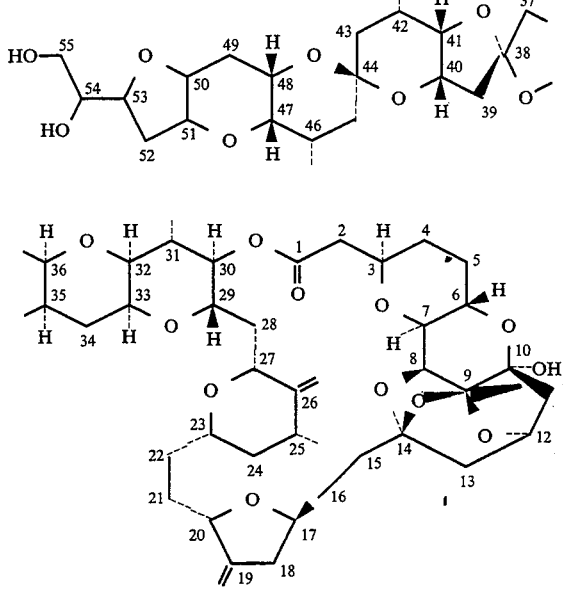

2. A composition of matter denominated halistatin 2 and having the following NMR assignments:

| | $^{13}$C(100 MHz) | XHCorr. (400 MHz) | HMBC(500 MHz) |
|---|---|---|---|
| 1 | 172.86p | | H-2,H-30 |
| 2 | 41.19p | 2.55 dd(10,18); 2.46 brd(18) | |
| 3 | 75.00n | 3.91 | H-2 |
| 4 | 31.61p | | |
| 6 | 71.20n | 4.45 | H-7,H-8 |
| 7 | 78.84n | 3.05 dd(1.8,9.7) | H-8 |
| 8 | 75.16n | 4.24 | H-7,H-9 |
| 9 | 79.77n | 3.74 brd(4.4) | H-8,H-11,H-12 |
| 10 | 103.75p | | H-8,H-9,H-11,H-12 |
| 11 | 87.64n | 4.25 | H-9,H-12,H-13 |
| 12 | 82.29n | 4.73 t(4.6) | H-9,H-11,H-13 |
| 13 | 49.00p | 2.13;1.96 dd(5,13) | |
| 14 | 110.83p | | H-8,H-11,H-12,H-13 |
| 16 | 29.37p | 2.17;1.40 | H-18 |
| 17 | 77.18n | 4.07 | H-18 |
| 18 | 39.75p | 2.80 brm;2.32 | H-19a |
| 19 | 153.16p | | H-18,H-17,H-19a |
| 19a | 105.65p | 5.05 brs;5.00 brs | H-18 |
| 20 | 76.07n | 4.45 | H-19a |
| 23 | 75.45n | 3.69 brt(10) | |
| 24 | 44.96p | 1.72;1.02 | H-25a |
| 25 | 37.22n | 2.32 | H-25a,H-24,H-26a |
| 25a | 18.41n | 1.08 d(6.4) | H-24 |
| 26 | 153.32p | | H-27,H-25,H-25a,H-24,H-26a |
| 26a | 104.79p | 4.86 brs;4.80 brs | H-27,H-28 |
| 27 | 75.07n | 3.60 | H-29,H-26a |
| 28 | 37.90p | 2.25;1.80 | H-29,H-30 |
| 29 | 73.78n | 4.23 | H-27,H-25 |
| 30 | 77.56n | 4.62 dd(4.7,7.6) | H-29,H-31a |
| 31 | 37.50n | 2.05 | H-29,H-31a |
| 31a | 15.76n | 1.04 d(7.1) | H-30,H-31,H-32 |
| 32 | 78.20n | 3.20 dd(4.9,6.7) | H-30,H-31a,H-33 |
| 33 | 65.95n | 3.88 | H-29,H-32 |
| 34 | 30.85p | 2.04;1.80 | H-33,H-36 |
| 35 | 76.34n | 4.10 | H-36 |
| 36 | 78.01n | 4.10 | H-35 |
| 37 | 45.51p | 2.39;2.00 | |
| 38 | 114.78p | | H-36,H-37,H-39,H-40 |
| 39 | 44.84p | 2.30;2.30 | |
| 40 | 72.31n | 3.94 brs | H-39,H-41 |
| 41 | 81.06n | 3.65 brt(2.8) | H-42a,H-39 |
| 42 | 27.15n | 2.36 | H-42a,H-43 |
| 42a | 18.18n | 0.94 d(7.0) | H-43 |
| 43 | 38.09p | 1.43;1.33 | H-42a,H-41 |
| 44 | 98.14p | | H-43 |
| 45 | 38.17p | | H-46a,H-47 |
| 46 | 30.14n | 2.18 | H-46a,H-47 |
| 46a | 17.65n | 0.93 d(6.8) | H-47 |
| 47 | 74.57n | 3.11 brd(2.2) | H-46a |
| 48 | 65.31n | 3.57 | H-47 |
| 49 | 32.03p | 2.10;1.92 | H-48 |
| 50 | 75.81n | 3.86 | H-48,H-51 |
| 51 | 78.44n | 4.01 brs | H-47,H-50 |
| 52 | 37.29p | 2.02; | |
| 53 | 79.87n | 4.24 | H-55,H-51 |
| 54 | 75.16n | 3.49 brdd(5.5,10) | H-55 |
| 55 | 65.18p | 3.56 brs;3.56 brs | |

* * * * *